(12) United States Patent
Furukawa et al.

(10) Patent No.: US 12,054,650 B2
(45) Date of Patent: Aug. 6, 2024

(54) ADHESIVE FOR ENDOSCOPE AND CURED PRODUCT THEREOF, AND ENDOSCOPE AND METHOD FOR PRODUCING THE SAME

(71) Applicant: FUJIFILM Corporation, Tokyo (JP)

(72) Inventors: Kazushi Furukawa, Ashigarakami-gun (JP); Yoshihiro Nakai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 772 days.

(21) Appl. No.: 17/144,393

(22) Filed: Jan. 8, 2021

(65) Prior Publication Data

US 2021/0189203 A1 Jun. 24, 2021

Related U.S. Application Data

(63) Continuation of application No. PCT/JP2019/026066, filed on Jul. 1, 2019.

(30) Foreign Application Priority Data

Jul. 10, 2018 (JP) ................................ 2018-131088

(51) Int. Cl.
  *C09J 163/04* (2006.01)
  *A61B 1/00* (2006.01)
  *C09J 11/06* (2006.01)

(52) U.S. Cl.
  CPC ........... *C09J 163/04* (2013.01); *A61B 1/0011* (2013.01); *C09J 11/06* (2013.01)

(58) Field of Classification Search
  CPC ........ C09J 129/04; C09J 163/04; C08K 5/053
  See application file for complete search history.

(56) References Cited

U.S. PATENT DOCUMENTS

| | | | |
|---|---|---|---|
| 4,115,360 | A | 9/1978 | Schulze et al. |
| 5,773,139 | A | 6/1998 | Ogura et al. |
| 2015/0240137 | A1 | 8/2015 | Yokoyama et al. |
| 2019/0082937 | A1 | 3/2019 | Hayashi et al. |

FOREIGN PATENT DOCUMENTS

| | | | | |
|---|---|---|---|---|
| CN | 104781364 A | | 7/2015 | |
| JP | 54-154500 A | | 12/1979 | |
| JP | 1-304165 A | | 12/1989 | |
| JP | 01304165 A | * | 12/1989 | |
| JP | 7-256831 A | | 10/1995 | |
| JP | 07256831 A | * | 10/1995 | ............. B32B 27/08 |

(Continued)

OTHER PUBLICATIONS

Machine-generated English-language translation of JP-2015093948-A.*

(Continued)

*Primary Examiner* — Vu A Nguyen
(74) *Attorney, Agent, or Firm* — Sughrue Mion, PLLC

(57) ABSTRACT

Provided are an adhesive for an endoscope and a cured product thereof. The adhesive for an endoscope includes an epoxy resin including at least one of a bisphenol A epoxy resin, a bisphenol F epoxy resin, or a phenol novolac epoxy resin, a polyamine compound, and an alcohol compound. Also provided are an endoscope in which the cured product is fixed and a method for producing the endoscope.

10 Claims, 3 Drawing Sheets

(56) References Cited

FOREIGN PATENT DOCUMENTS

| JP | 2011-12144 A | 1/2011 |
|----|----|----|
| JP | 2014-210836 A | 11/2014 |
| JP | 2015-093948 A | 5/2015 |
| JP | 2015093948 A * | 5/2015 |
| JP | 2017-214546 A | 12/2017 |

OTHER PUBLICATIONS

Machine-generated English-language translation of JP-07256831-A.*

Machine-generated English-language translation of JP-01304165-A.*

Huntsman Jeffamine D-230 Datasheet (Year: 2015).*

Chinese Office Action issued Jul. 12, 2023 in Application No. 201980042122.8.

Extended European Search Report dated Aug. 16, 2021 in European Application No. 19834002.8.

International Search Report dated Sep. 17, 2019 from the International Searching Authority in International Application No. PCT/JP2019/026066.

Written Opinion dated Sep. 17, 2019 from the International Bureau in International Application No. PCT/JP2019/026066.

International Preliminary Report on Patentability dated Jan. 10, 2021 from the International Bureau in International Application No. PCT/JP2019/026066.

Communication dated Apr. 26, 2022, issued in corresponding Japanese Application No. 2020-530117.

Office Action dated Oct. 19, 2021 from the Japanese Patent Office in corresponding JP Application No. 2020-530117.

* cited by examiner

ADHESIVE FOR ENDOSCOPE AND CURED PRODUCT THEREOF, AND ENDOSCOPE AND METHOD FOR PRODUCING THE SAME

CROSS-REFERENCE TO RELATED APPLICATIONS

This application is a Continuation of PCT International Application No. PCT/JP2019/026066 filed on Jul. 1, 2019, which claims priority under 35 U.S.C. § 119 (a) to Japanese Patent Application No. 2018-131088 filed in Japan on Jul. 10, 2018. Each of the above applications is hereby expressly incorporated by reference, in its entirety, into the present application.

BACKGROUND OF THE INVENTION

1. Field of the Invention

The present invention relates to an adhesive for an endoscope and a cured product thereof, and an endoscope and a method for producing the endoscope.

2. Description of the Related Art

Endoscopes for examining human body cavities are repeatedly used. Thus, a flexible tube constituting an insertion section of an endoscope is washed and disinfected with chemicals after each use. In particular, when an endoscope is inserted into a highly susceptible region, such as a bronchus, cleanliness at the level of sterilization higher than disinfection is required. Therefore, endoscopes are required to have high resistance to repeated sterilization treatments, for example, with hydrogen peroxide plasma.

The insertion section of an endoscope is inserted into a body cavity through the oral cavity, the nasal cavity, or the like. To alleviate foreign body sensation and pain in patients during the insertion, the insertion section of an endoscope desirably has a smaller diameter. Thus, instead of bulky members such as screws, adhesives are mainly used to bond together members constituting the insertion section.

Among the adhesives, epoxy adhesives have high workability, and cured products thereof are excellent in adhesiveness, electrical properties, heat resistance, moisture resistance, and other properties. Thus, epoxy adhesives are used in various fields, and use thereof to fix constituent members of an endoscope is also under consideration.

For example, JP2014-210836A discloses an adhesive composition containing a base resin including acrylic rubber and an epoxy resin selected from the group consisting of bisphenol A epoxy resins, bisphenol F epoxy resins, and phenol novolac epoxy resins, a curing agent including xylylenediamine, a filler including silica, and an ion exchanger. JP2014-210836A states that an adhesive layer formed by curing the adhesive composition retains high adhesive strength and is less likely to undergo degradation in appearance if subjected to a sterilization treatment with hydrogen peroxide plasma.

SUMMARY OF THE INVENTION

As described above, adhesives are often used to fix constituent members of an endoscope. However, cured products of adhesives generally have tendency to be poor in physical or chemical stability. Thus, if an adhesive is used to fix a member in producing an instrument subjected to high-temperature washing and a powerful sterilization treatment, such as an endoscope, a decrease in performance of the instrument is likely to occur due to repeated use.

When an adhesive is used to bond an optical member (e.g., a lens or a prism) of an endoscope, optical properties that can sufficiently maintain the transparency of an adhesive joint are also required. To secure the transparency, it is important to increase the compatibility between components constituting the adhesive.

As described above, JP2014-210836A discloses a technique for increasing the resistance of an adhesive layer formed of an epoxy adhesive to hydrogen peroxide plasma sterilization treatment. In this technique, the epoxy adhesive is allowed to react in a relatively high temperature range (60° C. to 135° C.) to sufficiently increase the cure speed and the cure rate, thus achieving the above-described sterilization resistance.

However, in producing an endoscope, which is a precision medical instrument, a curing reaction of an adhesive in a high temperature range may cause a problem with a constituent member (precision device). Thus, an adhesive used to produce an endoscope is required to have the property of curing quickly even in a lower temperature range. It is also required that the cure rate (crosslink density) in a low temperature range be sufficiently increased to achieve the property of being less likely to degrade if subjected to a sterilization treatment, for example, with hydrogen peroxide plasma. However, the technique disclosed in JP2014-210836A and other adhesives for endoscopes of the related art have not sufficiently satisfied the above-described properties (both a quick cure speed in a low temperature range and high sterilization treatment resistance of a cured product obtained by low temperature curing reaction).

An object of the present invention is to provide an adhesive for an endoscope and a cured product of the adhesive. The adhesive is suitable for fixing a constituent member of an endoscope. The adhesive can be quickly cured even in a low temperature range, and a cured product obtained by the curing reaction has sufficient transparency and high resistance to repeated sterilization treatments. Another object of the present invention is to provide an endoscope that is less likely to undergo a decrease in performance if repeatedly subjected to a sterilization treatment and a method for producing the endoscope.

To achieve the above objects, the present inventors conducted intensive studies and found the following: when an epoxy adhesive includes a polyamine compound as a curing component to be combined with a base epoxy resin and further includes an alcohol compound in combination, the alcohol compound exhibits an excellent cure accelerating effect, and the adhesive cures quickly even in a low temperature range; the components of the adhesive exhibit good compatibility with each other, and a cured product exhibits sufficient transparency; and, in addition, the cured product is less likely to degrade if subjected to repeated sterilization treatments, for example, with hydrogen peroxide plasma. The present invention has been completed by further conducting studies based on these findings.

The above objects have been achieved by the following means.

[1]

An adhesive for an endoscope includes an epoxy resin including at least one of a bisphenol A epoxy resin, a bisphenol F epoxy resin, or a phenol novolac epoxy resin, a polyamine compound, and an alcohol compound.

[2]

In the adhesive for an endoscope according to [1], the alcohol compound has a hydroxyl equivalent of 25 to 150.

[3]

In the adhesive for an endoscope according to [1] or [2], the alcohol compound has a molecular weight of 50 to 500.

[4]

In the adhesive for an endoscope according to [1] or [2], the alcohol compound is a polymer and has a number average molecular weight of 2,000 to 100,000.

[5]

In the adhesive for an endoscope according to any one of [1] to [4], the alcohol compound has a C Log P of −1.5 to 3.5.

[6]

In the adhesive for an endoscope according to any one of [1] to [5], the alcohol compound is a polyol compound.

[7]

In the adhesive for an endoscope according to any one of [1] to [6], the polyamine compound has an active hydrogen equivalent of 10 to 2,000.

[8]

In the adhesive for an endoscope according to any one of [1] to [7], the polyamine compound has a polyoxyalkylene structure.

[9]

In the adhesive for an endoscope according to any one of [1] to [8], relative to 100 parts by mass of a content of the epoxy resin, a content of the polyamine compound is 5 to 60 parts by mass, and a content of the alcohol compound is 1 to 20 parts by mass.

[10]

A cured product is formed by curing the adhesive for an endoscope according to any one of [1] to [9].

[11]

An endoscope includes the cured product according to [10] and a constituent member fixed with the cured product.

[12]

A method for producing an endoscope includes fixing a constituent member by using the adhesive for an endoscope according to any one of [1] to [9].

In the description of the present invention, "to" is meant to include the numerical values before and after "to" as the lower and upper limits.

The adhesive for an endoscope according to the present invention can be quickly cured even in a low temperature range, and a cured product obtained by the curing reaction exhibits sufficient transparency and also has high resistance to repeated sterilization treatments. The cured product according to the present invention exhibits sufficient transparency and also has high resistance to repeated sterilization treatments. Therefore, the endoscope according to the present invention including the cured product as a member for fixing a constituent member has high optical performance and is less likely to undergo a decrease in performance if repeatedly subjected to a sterilization treatment. According to the method for producing an endoscope according to the present invention, an endoscope that has high optical performance and is less likely undergo degradation in performance if repeatedly subjected to a sterilization treatment can be obtained.

DESCRIPTION OF THE PREFERRED EMBODIMENTS

Adhesive for Endoscope

Figure 1:
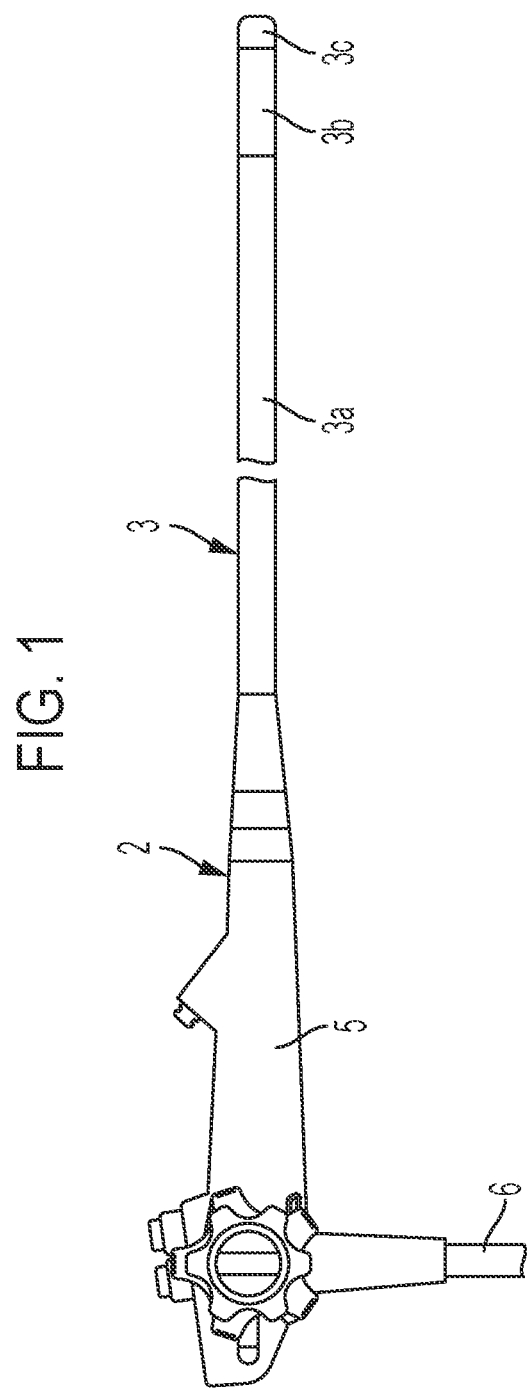
FIG. 1 is an external view illustrating a configuration of an endoscope according to an embodiment of the present invention.

A preferred embodiment of an adhesive for an endoscope according to the present invention will be described.

The adhesive for an endoscope according to the present invention (hereinafter also referred to as "the adhesive according to the present invention") includes (A) an epoxy resin, (B) a polyamine compound, and (C) an alcohol compound, and the epoxy resin includes at least one of a bisphenol A epoxy resin, a bisphenol F epoxy resin, or a phenol novolac epoxy resin.

The epoxy resin is a base resin of the adhesive, and the polyamine compound is a curing component that reacts with the epoxy resin to cure the adhesive. The alcohol compound acts as a cure accelerating component that accelerates the above curing reaction.

The adhesive for an endoscope according to the present invention may be in any form as long as the above components are included. For example, the adhesive for an endoscope according to the present invention may contain a mixture of the components (A) to (C) (one-component type), or may include the components (A) to (C) with one of the components (A) to (C) being separated from the other components (two-component type). Alternatively, the adhesive for an endoscope according to the present invention may include the components (A) to (C) with the components (A) to (C) being separated from each other (three-component type). Any of these types are included in the adhesive according to the present invention.

When the contents of the components in the adhesive are described in this specification or the contents of the components in the adhesive are specified in the present invention, in the form of a two-component or three-component adhesive, mixing of the components (A) to (C) at the point of use is meant to be performed such that each component satisfies the above desired content in the mixture. That is, in the form of a two-component or three-component adhesive, the contents of the components (A) to (C) need not satisfy the contents described in this specification or the contents specified in the present invention in a state where the components are separated from each other. It means that in the form of a two-component or three-component adhesive, the contents described in this specification or the contents specified in the present invention are satisfied when the components (A) to (C) are mixed together at the point of use.

When the adhesive for an endoscope according to the present invention is a one-component adhesive, or when the adhesive is a two-component or three-component adhesive in which components that can react with each other are mixed together (e.g., an epoxy resin and a polyamine compound are mixed together), the adhesive is preferably preserved at a low temperature at which level substantially no reaction occurs, in order to keep the components stably maintained with no reaction occurring or with reaction sufficiently inhibited. For example, the adhesive can be preserved at −20° C. or lower, and is preserved preferably at −30° C. or lower, more preferably at −40° C. or lower, still more preferably at −50° C. or lower. If necessary, the adhesive can be preserved in darkness.

The adhesive according to the present invention can include, for example, a solvent, a plasticizer, an adhesion improver (e.g., a silane coupling agent), a surfactant, a colorant (e.g., a pigment or a dye), a weathering agent, an antioxidant, a heat stabilizer, a lubricant, an antistatic agent, a whitener, a release agent, a conductive agent, a viscosity regulator, a filler (e.g., silica or calcium carbonate), a thixotropy-imparting agent, a diluent, and a flame retardant, as long as the advantageous effects of the present invention are not impaired.

The adhesive according to the present invention, even if cured in a low temperature range (e.g., lower than 60° C., preferably 0° C. to 50° C.), provides a cured product having high resistance to repeated sterilization treatments, for example, with hydrogen peroxide plasma. Although not clear, the reasons for this are presumably as follows.

That is, the adhesive according to the present invention contains an alcohol compound as well as a polyamine compound. Thus, for example, an alcoholic hydroxyl group of the alcohol compound acts on an epoxy group of the epoxy resin to activate the epoxy group, and as a result, the curing reaction between the epoxy resin and the polyamine compound proceeds quickly even in a low temperature range; and due to the above action of the alcohol compound, the curing reaction can further proceed at the late stage of the low-temperature curing reaction to provide a cured product having a highly increased crosslink density. These are probably the reasons.

The adhesive according to the present invention is used to fix various members constituting an endoscope (endoscope-constituting members). That is, the adhesive according to the present invention is used to bond an endoscope-constituting member to another constituent member of the endoscope to thereby fix the constituent member of the endoscope to the other constituent member of the endoscope. The adhesive used to fix the endoscope-constituting member is cured and constitutes an adhesive joint of the endoscope.

The member fixed using the adhesive according to the present invention is preferably, but not necessarily, a metal member, a glass member, a resin member, or the like. The "fixing" of an endoscope-constituting member is performed by bonding the endoscope-constituting member to another member (supporting member) constituting the endoscope. The supporting member may be a tube wall or the like of the endoscope or an immovable member fixed to the tube wall or the like, or may be a member whose relative position in the endoscope can be moved like a tube. In the present invention, the term "fixing" is meant to include filling, that is, sealing a space between an endoscope-constituting member and a supporting member incorporated with the endoscope-constituting member with a cured product of an adhesive.

The components constituting the adhesive according to the present invention will be described below.

(A) Epoxy Resin

The adhesive according to the present invention includes an epoxy resin, and the epoxy resin includes at least one of a bisphenol A epoxy resin, a bisphenol F epoxy resin, or a phenol novolac epoxy resin. The adhesive according to the present invention may include one or more epoxy resins selected from the group consisting of bisphenol A epoxy resins, bisphenol F epoxy resins, and phenol novolac epoxy resins.

The proportion of the total amount of bisphenol A epoxy resin, bisphenol F epoxy resin, and phenol novolac epoxy resin relative to the total amount of epoxy resin included in the adhesive according to the present invention is preferably 70 mass % or more, preferably 80 mass % or more, more preferably 90 mass % or more. More preferably, the epoxy resin included in the adhesive according to the present invention is at least one of a bisphenol A epoxy resin, a bisphenol F epoxy resin, or a phenol novolac epoxy resin.

The epoxy equivalent of the epoxy resin included in the adhesive according to the present invention is preferably 10 to 1,000, more preferably 50 to 500, still more preferably 80 to 400, particularly preferably 100 to 300. The epoxy resin included in the adhesive according to the present invention typically has two or more epoxy groups in one molecule.

The epoxy equivalent is a value obtained by dividing the molecular weight of an epoxy compound by the number of moles of epoxy groups of the epoxy compound.

The bisphenol A epoxy resin that can be used in the adhesive according to the present invention is not particularly limited and may be any bisphenol A epoxy resin commonly used as a base resin of an epoxy adhesive. Preferred specific examples include bisphenol A diglycidyl ethers (jER825, jER828, and jER834 (trade names) manufactured by Mitsubishi Chemical Corporation) and bisphenol A propoxylate diglycidyl ethers (manufactured by Sigma-Aldrich).

The bisphenol F epoxy resin that can be used in the adhesive according to the present invention is not particularly limited and may be any bisphenol F epoxy resin commonly used as a base resin of an epoxy adhesive. Preferred specific examples include bisphenol F diglycidyl ethers (trade name: EPICLON 830, manufactured by DIC Corporation) and 4,4'-methylenebis(N,N-diglycidylaniline).

The phenol novolac epoxy resin that can be used in the adhesive according to the present invention is not particularly limited and may be any phenol novolac epoxy resin commonly used as a base resin of an epoxy adhesive. Such a phenol novolac epoxy resin is marketed, for example, by Sigma-Aldrich under the product number 406775.

The content of the epoxy resin included in the adhesive according to the present invention may be 5 to 90 mass % and is more preferably 10 to 75 mass %.

(B) Polyamine Compound

The adhesive according to the present invention contains at least one polyamine compound. The polyamine compound included in the adhesive according to the present invention is a compound having, in one molecule, two or more amino groups having active hydrogen. The polyamine compound preferably has an unsubstituted amino group (—$NH_2$), more preferably has two or more unsubstituted amino groups. Still more preferably, the polyamine compound is a primary polyamine compound (polyamine compound in which all amino groups are unsubstituted amino groups). In the adhesive according to the present invention, a wide variety of polyamine compounds that exhibit curing action in epoxy adhesives can be used.

The number of amino groups having active hydrogen in one molecule of the polyamine compound is preferably 2 to 10, more preferably 2 to 8, still more preferably 2 to 6, further more preferably 2 to 4, particularly preferably 2 or 3. In particular, at least one selected from the group consisting of diamine compounds and triamine compounds is suitable for use.

The active hydrogen equivalent (equivalent of active hydrogen of amino groups) of the polyamine compound (B) is preferably 10 to 2,000, more preferably 20 to 1,000, still more preferably 30 to 900, further more preferably 40 to 800, yet more preferably 60 to 700, particularly preferably 65 to 600.

The active hydrogen equivalent is a value obtained by dividing the molecular weight of the polyamine compound by the number of moles of active hydrogen of amino groups of the polyamine compound (i.e., a molecular weight of one active hydrogen of an amino group in the polyamine compound).

The molecular weight of the polyamine compound is preferably 100 to 6,000, more preferably 100 to 3,000. When the polyamine compound is a polymer (e.g., when the polyamine compound has a polyoxyalkylene group described below), the molecular weight is a number average molecular weight.

In the polyamine compound, two or more amino groups are preferably bonded together through a group selected from the group consisting of aliphatic hydrocarbon groups, alicyclic hydrocarbon groups, aromatic hydrocarbon groups, and heterocyclic groups or a combination thereof. These groups may have a heteroatom such as an oxygen atom, a nitrogen atom, or a sulfur atom (preferably an oxygen atom) between carbon-carbon bonds.

In particular, to provide a cured product with higher flexibility and stronger physical properties, the polyamine compound preferably has, in its molecule, a linear alkylene group or a polyoxyalkylene group, more preferably a polyoxyalkylene group.

The polyamine compound having a linear alkylene group is preferably an alkylenediamine compound. The polyamine compound having a polyoxyalkylene group is more preferably a polyoxyalkylenediamine compound or a polyoxyalkylenetriamine compound.

The above linear alkylene group may be linear or branched, and the number of carbon atoms in the linear alkylene group is preferably 1 to 20, more preferably 5 to 12. Specific examples of alkylene groups methylene, ethylene, hexamethylene, 2,4,4-trimethylhexamethylene, 2-methylpentamethylene, and dodecamethylene.

The alkylene group in the above polyoxyalkylene group may be a linear alkylene group or a branched alkylene group. The number of carbon atoms in the alkylene group in the above polyoxyalkylene group is preferably 1 to 10, more preferably 2 to 6, still more preferably 2 to 4.

The above polyoxyalkylene group is more preferably a polyoxyethylene group or a polyoxypropylene group.

A plurality of oxyalkylene groups of the above polyoxyalkylene group may be the same as or different from each other. The average number of repetitions of an oxyalkylene group of the above polyoxyalkylene group is preferably 2 to 1,000, more preferably 3 to 500. The average number of repetitions may also be 2 to 100, 2 to 50, 2 to 35, or 2 to 25.

When the above polyoxyalkylene group has a plurality of different oxyalkylene groups, the average number of repetitions of the oxyalkylene groups is the sum of the average number of repetitions of each oxyalkylene group. For example, the average number of repetitions in B-12 below is 2+9+2=13, and the average number of repetitions in B-15 below is 2+2+2=6.

Preferred specific examples of the polyamine compound that can be used in the present invention are shown below. The number attached to parentheses is the average number of repetitions of the repeating unit in the parentheses.

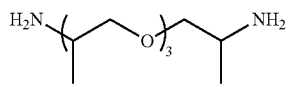
B-1

-continued

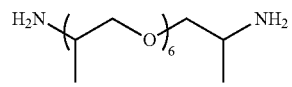
B-2

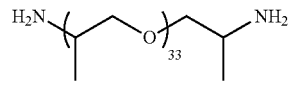
B-3

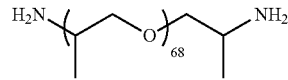
B-4

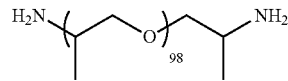
B-5

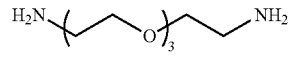
B-6

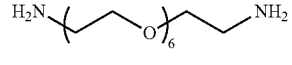
B-7

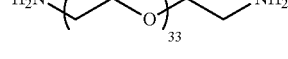
B-8

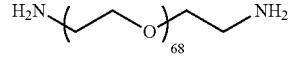
B-9

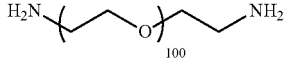
B-10

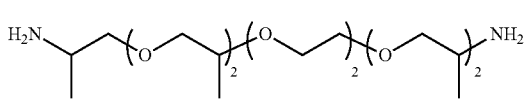
B-11

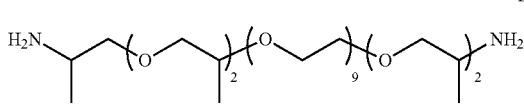
B-12

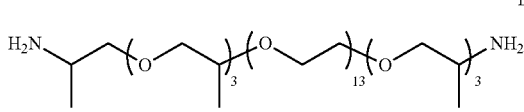
B-13

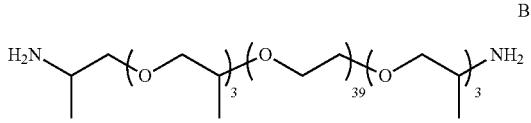
B-14

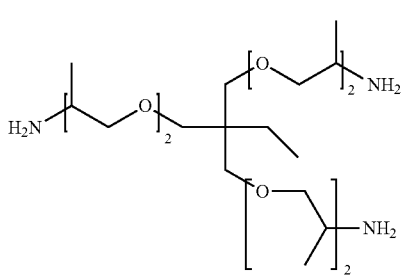
B-15

B-16
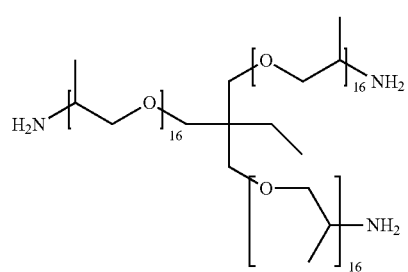
B-17
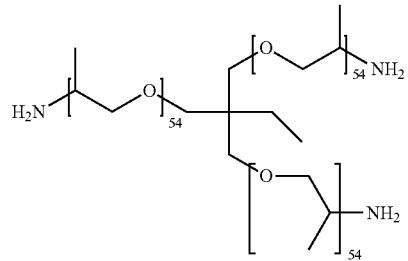
B-18
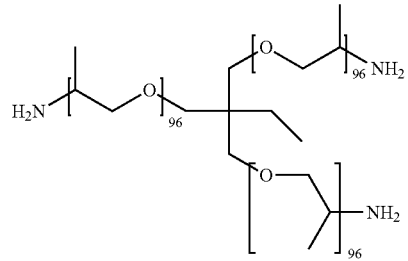
B-19
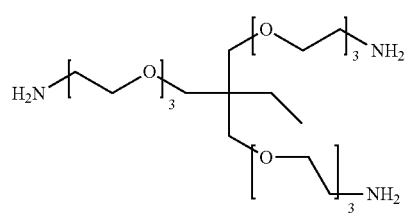
B-20
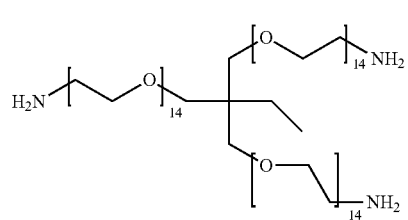
B-21
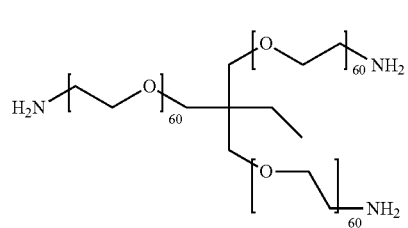
B-22
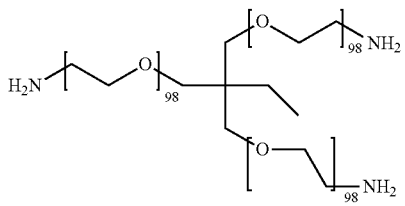
B-23
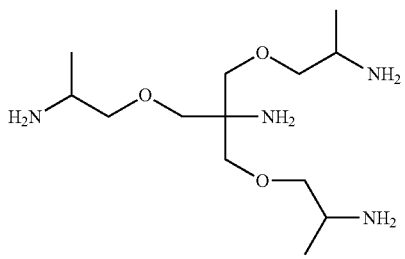
B-24
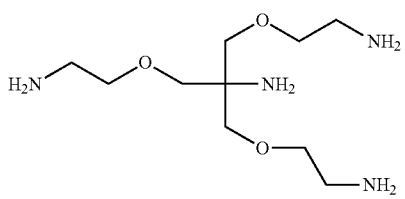
B-25
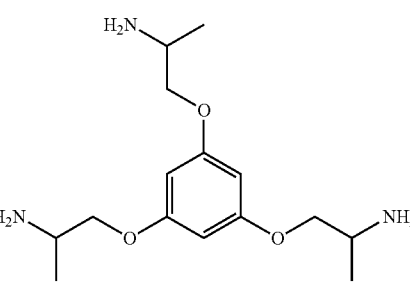
B-26
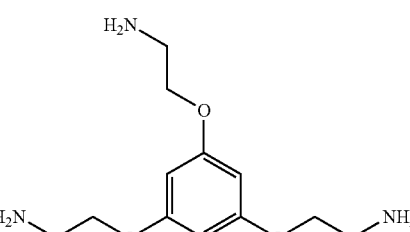
B-27
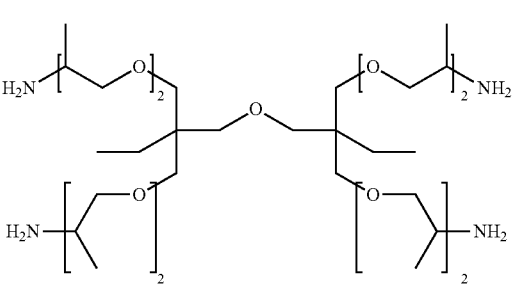

B-28
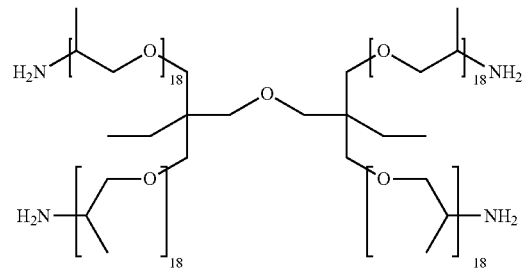
B-29
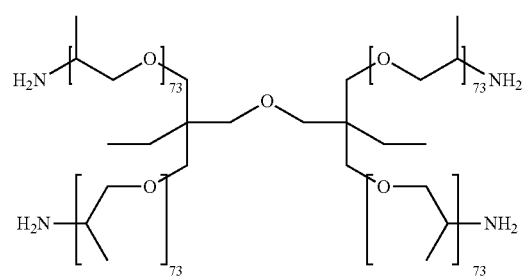
B-30
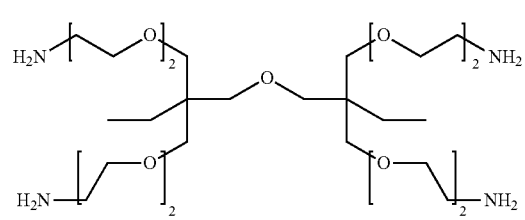
B-31
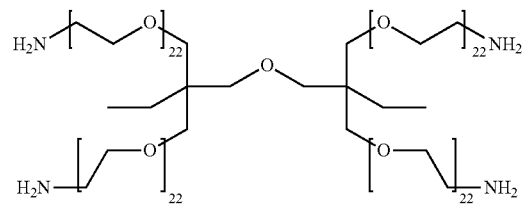
B-32
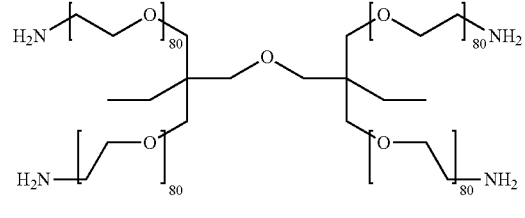
B-33
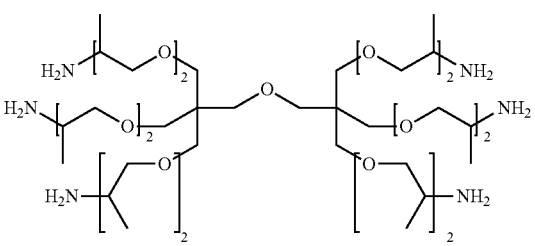
B-34
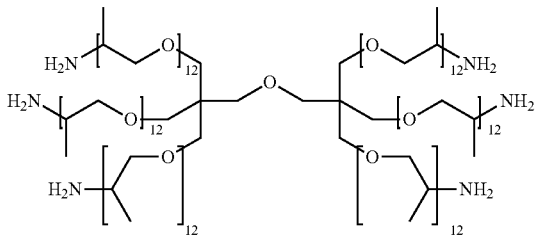
B-35
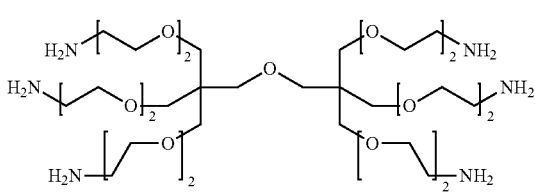
B-36
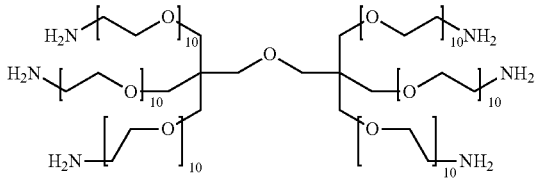
B-37
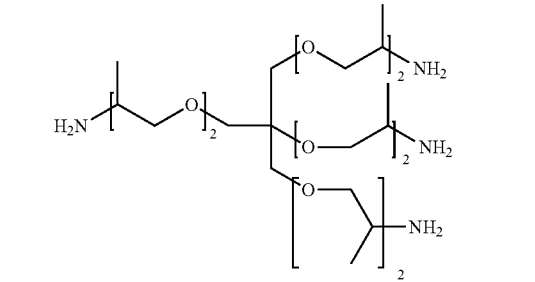
B-38
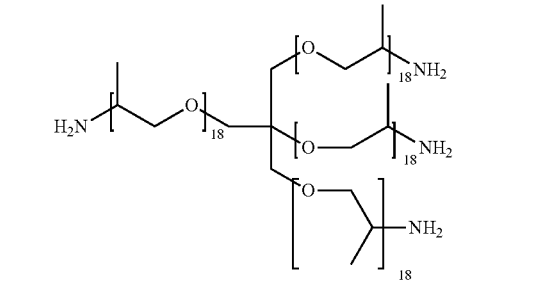
B-39
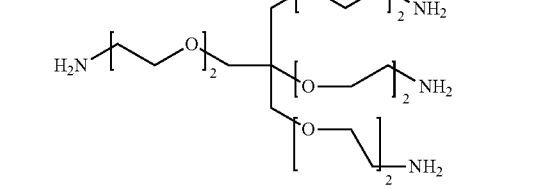

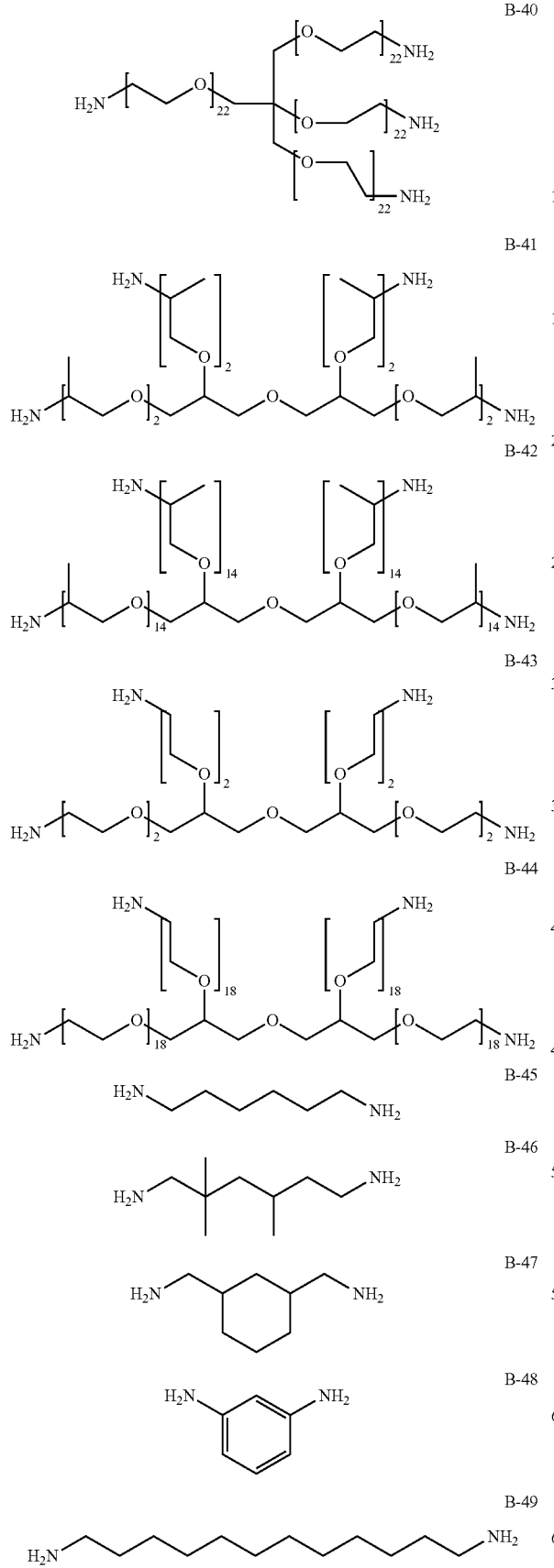

The polyamine compound can be synthesized by a usual method. Alternatively, a commercially available product may be used.

In the adhesive according to the present invention, the content of the polyamine compound can be appropriately set taking into account, for example, the active hydrogen equivalent of the polyamine compound. For example, the content of the polyamine compound relative to 100 parts by mass of the epoxy resin may be 5 to 300 parts by mass, and is more preferably 10 to 250 parts by mass, still more preferably 15 to 220 parts by mass. The content of the polyamine compound relative to 100 parts by mass of the epoxy resin may also be 15 to 200 parts by mass, 15 to 150 parts by mass, 15 to 100 parts by mass, or 15 to 60 parts by mass.

The content of the polyamine compound relative to 100 parts by mass of the epoxy resin may also be 5 to 200 parts by mass, 5 to 150 parts by mass, 5 to 100 parts by mass, or 5 to 60 parts by mass.

The active hydrogen equivalent of the polyamine compound relative to the epoxy equivalent of the epoxy resin (active hydrogen equivalent/epoxy equivalent) is preferably 0.1 to 1.5, more preferably 0.3 to 1.0, still more preferably 0.5 to 1.0.

The adhesive according to the present invention may contain a curing component other than the polyamine compound, and the proportion of the polyamine compound in the whole curing component is preferably 80 mass % or more, more preferably 90 mass % or more. The whole curing component may be constituted by the polyamine compound. When the adhesive according to the present invention includes a curing component other than the polyamine compound, the curing component may be any curing agent or curing aid known as a curing component of an epoxy adhesive. For example, at least one of an acid anhydride compound, an imidazole compound, a phosphorus compound, a thiol compound, a dicyandiamide compound, or a phenolic compound may be used in combination with the polyamine compound.

(C) Alcohol Compound

The adhesive according to the present invention contains at least one alcohol compound. The alcohol compound used in the adhesive according to the present invention may be any compound having an alcoholic hydroxyl group. This alcohol compound may be a primary alcohol, a secondary alcohol, a tertiary alcohol, or a combination thereof. To readily approach an epoxy group and more effectively produce a cure accelerating effect, the adhesive according to the present invention preferably includes at least a primary alcohol (compound having at least one —$CH_2$—OH in its molecule).

The alcohol compound may have a repeating structure such as an oligomer structure or a polymer structure or may be a low-molecular-weight compound not having such a structure. Two or more such alcohol compounds may be used in combination.

The number of alcoholic hydroxyl groups of the alcohol compound used in the adhesive according to the present invention may be one or more. In particular, for a greater cure accelerating effect, the hydroxyl equivalent (equivalent of alcoholic hydroxyl groups) of the alcohol compound used in the adhesive according to the present invention is preferably 25 to 150, more preferably 30 to 120, still more preferably 40 to 100. The hydroxyl equivalent is a value obtained by dividing the molecular weight of the alcohol compound by the number of moles of alcoholic hydroxyl groups of the alcohol compound (which means a molecular weight per alcoholic hydroxyl group of the alcohol compound).

The alcohol compound used in the present invention is preferably a polyol compound.

When the alcohol compound included in the adhesive according to the present invention is a low-molecular-weight compound as described above, the molecular weight thereof is preferably 50 or more and 500 or less (preferably less than 500), more preferably 60 or more and less than 500, still more preferably 70 or more and less than 300, particularly preferably 80 or more and less than 250. When the molecular weight is within this range, amino groups of the curing agent readily approach epoxy groups activated by the alcohol compound, cation polymerization of the epoxy groups, which is a side reaction, can be more effectively inhibited, and the curing reaction between the epoxy groups and the polyamine compound can be more effectively accelerated. When the molecular weight is within the above range, volatilization of the alcohol compound can be suppressed, and the solubility of the epoxy resin can be further increased.

When the alcohol compound included in the adhesive according to the present invention is a compound having an oligomer structure, the number average molecular weight thereof is preferably 500 or more and less than 2,000, more preferably 500 or more and less than 1,500, still more preferably 600 or more and less than 1,500. When the molecular weight is within this range, the density of alcoholic hydroxyl groups in a composition is further increased to efficiently cause activation of epoxy groups, and the curing reaction between the epoxy groups and the polyamine compound can be more effectively accelerated. When the molecular weight is within the above range, the solubility of the epoxy resin can be further increased, and the compatibility with a cured product can also be further increased.

When the alcohol compound included in the adhesive according to the present invention is a compound having a polymer structure, the number average molecular weight thereof is preferably 2,000 or more and 100,000 or less (preferably less than 100,000), more preferably 3,000 or more and 100,000 or less (preferably less than 100,000), still more preferably 5,000 or more and less than 50,000, particularly preferably 7,000 or more and less than 25,000. When the molecular weight is within this range, amino groups of the curing agent readily approach epoxy groups activated by the alcohol compound, cation polymerization of the epoxy groups, which is a side reaction, can be more effectively inhibited, and the curing reaction between the epoxy groups and the polyamine compound can be more effectively accelerated. When the molecular weight is within the above range, the solubility of the epoxy resin can be further increased, and the compatibility with a cured product can also be further increased.

In view of the compatibility with the epoxy resin, the alcohol compound included in the adhesive according to the present invention has a C Log P of preferably −1.5 or more and 3.5 or less, preferably −0.8 or more and 3.5 or less, more preferably −0.5 or more and 2.5 or less, still more preferably −0.4 or more and 2.0 or less, particularly preferably −0.3 or more and 1.4 or less.

The C Log P of the alcohol compound is a value determined using ChemDraw Ultra 13.0. When the alcohol compound is a compound not having a polymer structure, a calculated C Log P of the whole structural formula of the compound is used. When the alcohol compound is a compound having a polymer structure, the C Log P is determined as described below.

Case of Homopolymer

A calculated C Log P of the structural formula of a repeating unit is used. In this calculation, a linkage is replaced with a hydrogen atom.

Case of Copolymer

The C Log P of the structural formula of each copolymer component (monomer component) is calculated, and the C Log P obtained is multiplied by the copolymerization molar ratio (a number of more than 0 and less than 1) of each copolymer component. The sum of each obtained value (C Log P of copolymer component×copolymerization ratio of copolymer component) is used as a C Log P of the copolymer.

The alcohol compound preferably has, in its molecule, a group selected from the group consisting of aliphatic hydrocarbon groups, alicyclic hydrocarbon groups, aromatic hydrocarbon groups, and heterocyclic groups or a combination thereof. These groups may have a heteroatom such as an oxygen atom, a nitrogen atom, or a sulfur atom (preferably an oxygen atom) between carbon-carbon bonds.

In the present invention, the polyamine compound described above is not included in the definition of alcohol compound. That is, even if having an alcoholic hydroxyl group, a compound having, in one molecule, two or more amino groups having active hydrogen is classified as a polyamine compound in the present invention.

The alcohol compound is preferably not a secondary amine compound. The alcohol compound is preferably not a tertiary amine compound. That is, the alcohol compound preferably does not have a nitrogen atom.

Preferred specific examples of the alcohol compound are shown below, but the present invention is not limited to these examples.

Specific Examples of Low-Molecular-Weight Alcohol Compounds

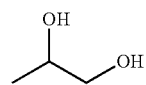

C-I-1

CLog P: −0.47

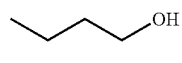

C-I-2

CLog P: 0.97

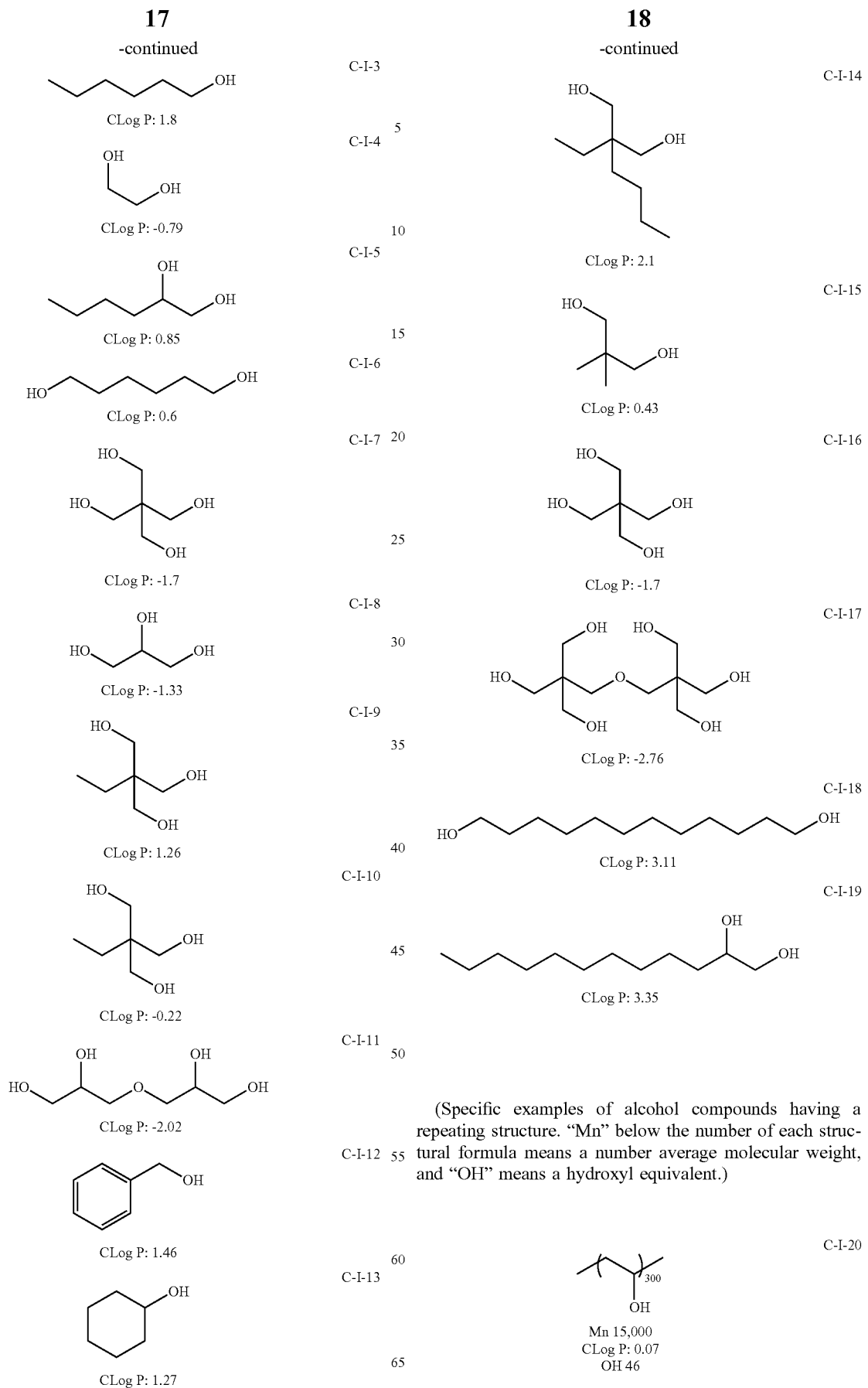
(Specific examples of alcohol compounds having a repeating structure. "Mn" below the number of each structural formula means a number average molecular weight, and "OH" means a hydroxyl equivalent.)

-continued

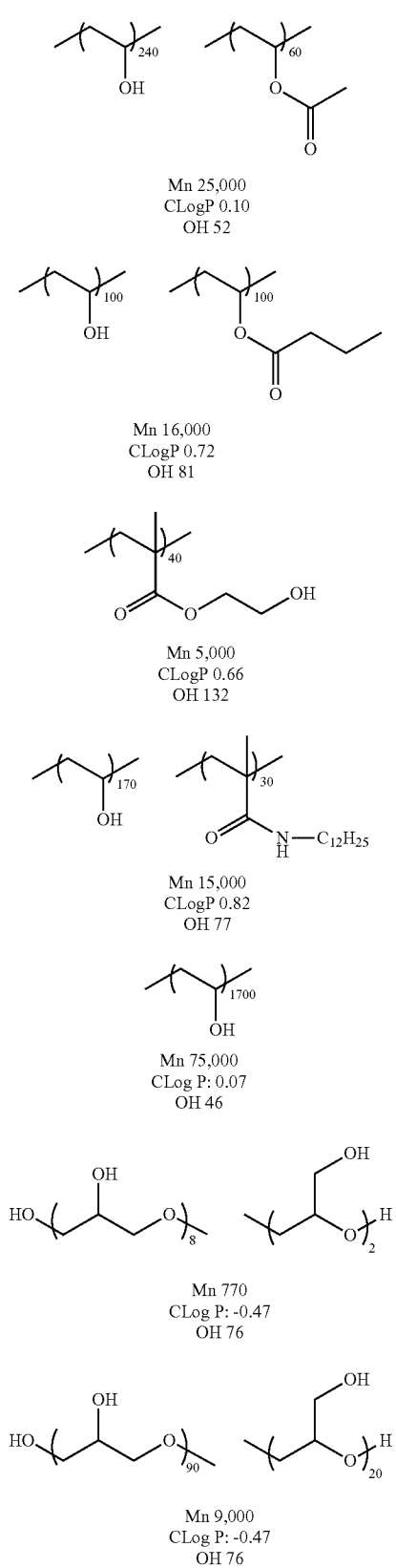

C-I-21

C-I-22

C-I-23

C-I-24

C-I-25

C-I-26

C-I-27

The numerical value attached to the parentheses of each structural formula is the average number of repetitions.

In the adhesive according to the present invention, the content of the alcohol compound can be appropriately set taking into account, for example, the hydroxyl equivalent of the alcohol compound. For example, the content of the alcohol compound relative to 100 parts by mass of the epoxy resin may be 1 to 20 parts by mass, and is more preferably 3 to 20 parts by mass, still more preferably 5 to 15 parts by mass.

Cured Product

A cured product according to the present invention is formed by curing the adhesive according to the present invention. That is, the cured product according to the present invention is used as a member constituting an adhesive joint of an endoscope. The curing temperature of the adhesive according to the present invention is not particularly limited. The adhesive according to the present invention can efficiently undergo a curing reaction even in a low temperature range to provide the cured product according to the present invention. Mixing of the components is preferably performed while removing bubbles, and thus is usually performed under reduced pressure. The curing temperature is preferably 100° C. or lower, more preferably 80° C. or lower, still more preferably 60° C. or lower, and may be 50° C. or lower. For the curing reaction to sufficiently proceed, the curing temperature is preferably 0° C. or higher, more preferably 10° C. or higher. The curing reaction time can be appropriately set depending on the intended use. Typically, the curing reaction is performed for 1.5 to 200 hours to obtain the cured product.

Endoscope

In an endoscope according to the present invention, a constituent member is fixed with the cured product according to the present invention. The phrase "a constituent member is fixed with the cured product according to the present invention" means that at least one member constituting the endoscope is fixed to a supporting member through the cured product according to the present invention.

An example of the endoscope (electronic endoscope) according to the present invention will be described. Electronic endoscopes are incorporated with a flexible tube for an endoscope (hereinafter a flexible tube for an endoscope may be referred to simply as a "flexible tube") and are widely used as medical instruments. In the example illustrated in FIG. 1, an electronic endoscope 2 includes an insertion section 3 to be inserted into a body cavity, a main-body operation section 5 connected to the proximal end portion of the insertion section 3, and a universal cord 6 to be connected to a processor device or a light source device. The insertion section 3 is composed of a flexible tube 3a connected to the main-body operation section 5, an angle portion 3b connected to the flexible tube 3a, and a tip portion 3c connected to the distal end of the angle portion 3b and mainly formed of a metal (e.g., stainless steel) member. An imaging device (not illustrated) for imaging a body cavity is built in the tip portion 3c. The flexible tube 3a, which occupies most of the length of the insertion section 3, is flexible over substantially the entire length thereof. In particular, a portion to be inserted into a body cavity or the like has a more flexible structure.

In FIG. 1, a plurality of channels (tubes, not illustrated) are formed that extend from the main-body operation section 5 to the distal end surface of the tip portion 3c through the insertion section 3 along the axis direction of the insertion section 3.

Figure 2:
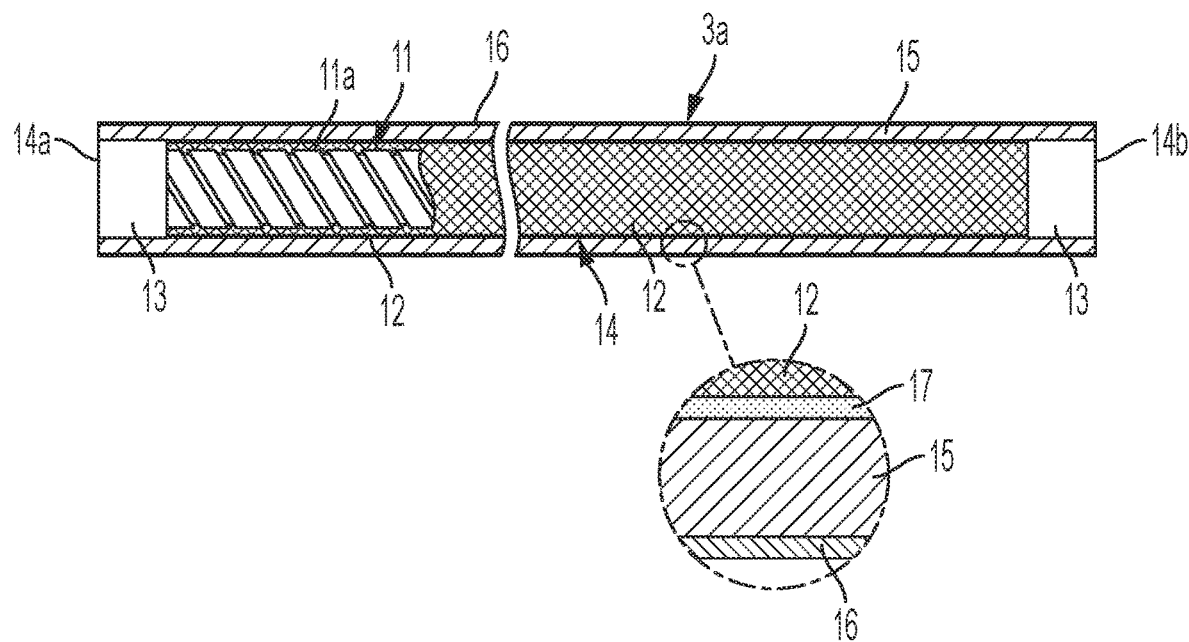
FIG. 2 is a partial sectional view illustrating a configuration of an insertion section of the endoscope illustrated in FIG. 1.

The flexible tube 3a in FIG. 1 is configured such that a resin layer 15 covers the outer peripheral surface of a flexible tube substrate 14, as illustrated in FIG. 2.

14a is the distal side (the tip portion 3c side), and 14b is the proximal side (the main-body operation section 5 side).

The flexible tube substrate 14 includes a spiral tube 11, which is disposed on the innermost side and formed by spirally winding a metal strip 11a, and a tubular net 12, which covers the spiral tube 11 and is formed by braiding metal wires. Caps 13 are fitted to opposite ends of the flexible tube substrate 14. The resin layer 15 is bonded to the flexible tube substrate 14 with an adhesive cured product layer 17 interposed therebetween. The adhesive cured product layer 17 can be formed by applying and curing the adhesive according to the present invention. While the adhesive cured product layer (adhesive joint) 17 is illustrated as a layer having a uniform thickness for convenience of illustration, the adhesive cured product layer 17 need not necessarily be in such a form and may be indeterminately interposed between the resin layer 15 and the flexible tube substrate 14. The adhesive cured product layer 17 may rather have substantially no thickness such that the resin layer 15 and the flexible tube substrate 14 are substantially directly bonded together.

The outer surface of the resin layer 15 is coated with a coat layer 16 having chemical resistance and containing, for example, fluorine. To clearly illustrate the layer structure, the adhesive cured product layer 17, the resin layer 15, and the coat layer 16 are illustrated as being thick relative to the diameter of the flexible tube substrate 14.

Figure 3:
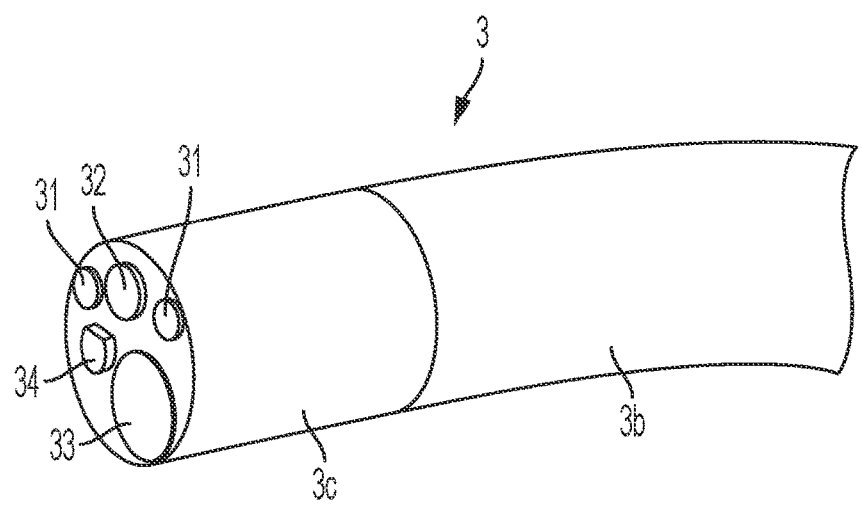
FIG. 3 is an external perspective view of a tip portion of the insertion section.

As illustrated in FIG. 3, an illumination window 31, an observation window 32, and a forceps port 33 are formed in the distal end surface of the tip portion 3c. To wash the distal end surface as required, a nozzle 34 for sending water and air is formed. The illumination window 31, the observation window 32, the forceps port 33, and the nozzle 34 communicate with the main-body operation section 5 through the channels.

Figure 4:
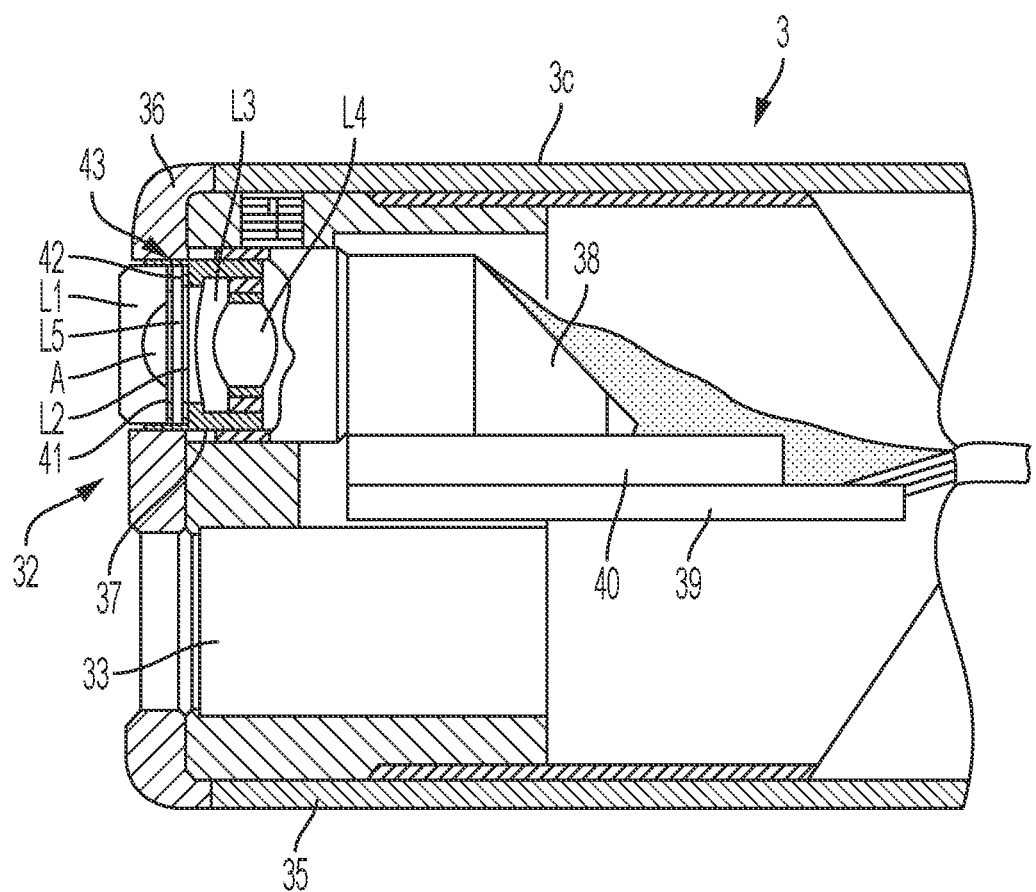
FIG. 4 is a partially cut-away partial sectional view of the tip portion, without hatching that shows sections of lenses and a prism.

As illustrated in FIG. 4, the tip portion 3c is composed of a tip-portion main body 35 made of metal and an end cap 36 made of an electrically insulating material.

An observation unit 43, which is an optical device, is disposed in the observation window 32. The observation unit 43 includes a lens holder 37, and in the lens holder 37, an objective optical system composed of lenses L1 to L5 is fixed with adhesive cured products 41 and 42. The adhesive cured products 41 and 42 can be formed by applying and curing the adhesive according to the present invention. In the objective optical system, A is an air layer. A prism 38 is bonded and fixed to an end face of the lens holder 37. The optical axis of the objective optical system can be bent at a right angle by the prism 38. The prism 38 is fixed to a solid-state imaging element 40. The solid-state imaging element 40 is fixed to a substrate 39. Also for the fixing of these components, the adhesive according to the present invention can be applied.

Method for Producing Endoscope

A method for producing an endoscope according to the present invention is not particularly limited as long as the method includes fixing an endoscope-constituting member by using the adhesive according to the present invention. For steps other than fixing of an endoscope-constituting member, usual production steps can be employed to produce the endoscope according to the present invention.

The endoscope-constituting member to be fixed may be made of any material, and may be, for example, a resin member, a metal member, or a glass member. The endoscope-constituting member can be fixed, for example, to a supporting member constituting the endoscope, for example, in the following manner. The components included in the adhesive according to the present invention are mixed together preferably under reduced pressure, and the resulting mixture is then injected or applied into or to a target portion and heated at −10° C. to 60° C. (preferably 0° C. to 60° C., more preferably 10° C. to 50° C.) for 1.5 to 200 hours.

Specific examples of how the adhesive is used in the method for producing an endoscope according to the present invention will be described below, but the present invention is not limited to these examples.

Examples of resin members among endoscope-constituting members fixed with the adhesive according to the present invention include tubes inserted into an insertion section of an endoscope. Examples of resin materials forming the tubes include fluorocarbon resins such as Teflon (registered trademark), polysulfone, polyester, polyolefin, and silicone. The adhesive according to the present invention can be used, for example, to bond a metal member or a glass member constituting an insertion section of an endoscope to any of the above tubes (to fix the metal member or the glass member to any of the above tubes).

As described above, the adhesive according to the present invention can also be used to form the adhesive cured product layer 17 in FIG. 2. The adhesive according to the present invention can also be used to bond together the resin layer 15 and the coat layer 16 in FIG. 2.

The adhesive according to the present invention can be used for outer-surface finishing and fixing of an end of a flexible outer cover tube (the resin layer 15) (the end on the distal side (the angle portion 3b side) of the flexible tube 3a). Specifically, a string is tightly bound around an end of the resin layer 15 of the flexible tube 3a to fix the resin layer 15 to the member thereinside, and then the adhesive is applied so as to coat the string and cured. The configuration in which the outermost layer on the distal-side end of the flexible tube 3a is formed of the adhesive according to the present invention reduces the likelihood of raveling of the string on the distal-side end and facilitates the insertion of the insertion section into a body cavity. The insertion section thus formed can maintain a bright appearance after sterilization.

The adhesive according to the present invention can be used for bonding of the tip portion 3c and the angle portion 3b and/or bonding of the insertion section 3 and the main-body operation section 5. For example, the tip portion 3c and the angle portion 3b are bonded together using the adhesive according to the present invention, after which a string is tightly wound around the adhesive joint between the tip portion 3c and the angle portion 3b and a portion near the adhesive joint to reinforce the bonding, and the adhesive is applied so as to coat the string and cured. The bonding of the insertion section 3 and the main-body operation section 5 is performed in the same manner.

The adhesive according to the present invention can also be used to fix various tubes inserted into the insertion section of the endoscope to the tip portion 3c and/or the main-body operation section 5.

The adhesive according to the present invention may also be used, at the tip portion 3c, to seal the illumination window 31 and the observation window 32 (to fix the glass members). A thick coating of the adhesive can smoothen the outer corners of the lenses and block the entrance of light from the lateral sides of the lenses.

The adhesive according to the present invention can be used to fix members, for example, to assemble the imaging device built in the tip portion 3c, to bond parts together, or to seal the solid-state imaging element 40. The imaging device has an optical system composed of a plurality of optical parts, such as the lenses L1 to L5 and the prism 38, and has the solid-state imaging element 40, such as a charge coupled device (CCD), that photoelectrically converts an optical image formed by the optical system into an imaging signal. The adhesive according to the present invention can be used, for example, for bonding of optical parts including the lenses L1 to L5 and the prism 38 made of materials such as glass and bonding of the lenses L1 to L5, the prism 38, and the like to the substrate 39 made of resin or metal. This bonding can fix the glass members and can fix the metal member.

The adhesive according to the present invention can be used for bond-fixing and sealing of the solid-state imaging element 40 and the substrate 39. This bonding can fix the metal members constituting the solid-state imaging element, the substrate, and the like.

As described above, the method for producing an endoscope according to the present invention includes a step of fixing an endoscope-constituting member by using the adhesive according to the present invention.

EXAMPLES

The present invention will now be described in more detail with reference to examples, but the examples should not be construed as limiting the present invention. "Room temperature" means 25° C. The amount of a component means the amount of the component itself. Specifically, when a raw material includes a solvent, the amount of the solvent is excluded.

Preparation Example: Preparation of Adhesive

An epoxy resin, a polyamine compound, and an alcohol compound shown in Tables below were mixed together at a mixing ratio shown in Tables below, and using a "THINKY MIXER ARV-310 (trade name, manufactured by THINKY CORPORATION)", the resulting mixture were defoamed for 5 minutes with stirring at 2,000 rpm under a reduced pressure of 1.0 Pa at room temperature to obtain an adhesive. In the following test examples, adhesives immediately after being prepared were used.

Test Examples

Initial Curability Test

Ten milliliters of the adhesive obtained in the above preparation example were poured into a 100 mL polypropylene disposable cup (manufactured by AS ONE Corporation) and allowed to sit at 30° C. The disposable cup was then tilted, and whether the adhesive flowed was visually checked. The time it took for the adhesive to stop flowing when the disposable cup was tilted was determined as a curing time, and initial curability was evaluated according to the following evaluation criteria.

Evaluation Criteria of Initial Curability

S: The curing time is less than 6 hours.

A: The curing time is 6 hours or more and less than 8 hours.

B: The curing time is 8 hours or more and less than 10 hours.

C: The curing time is 10 hours or more and less than 12 hours.

D: The curing time is 12 hours or more.

The results are shown in Tables below.

Compatibility (Transparency) Test

The adhesive obtained in the above preparation example was poured into a Teflon (registered trademark) mold of 50 mm long×5 mm wide×0.4 mm thick and allowed to sit at 30° C. for 12 hours to obtain a sheet-like sample (cured product).

On a sheet of paper on which black letters "TEST" and gray letters "TEST" were printed, the sheet-like sample was placed so as to cover the printed letters. The recognizability of the letters "TEST" were examined by visual observation from above the sheet-like sample to evaluate the compatibility of the adhesive components. As the compatibility between the components of the adhesive decreases, the sheet-like sample becomes white and hazy, and the recognizability of the letters decreases. The evaluation criteria of the compatibility are as follows.

Evaluation Criteria of Compatibility

A: The sheet-like sample is transparent, and both black printed letters and gray printed letters can be recognized without any problem.

B: A slight haze is observed in the sheet-like sample, but both black printed letters and gray printed letters can be recognized without any problem.

C: A haze is observed in the sheet-like sample and gray printed letters are difficult to recognize, but black printed letters can be recognized without any problem.

D: The sheet-like sample is whitened, and neither black printed letters nor gray printed letters can be recognized.

The results are shown in Tables below.

Sterilization Treatment Resistance Test

The adhesive obtained in the above preparation example was poured into a Teflon (registered trademark) mold of 50 mm long×5 mm wide×0.4 mm thick and allowed to sit at 30° C. for 170 hours to obtain a sheet-like sample (cured product).

Using a STERRAD (registered trademark) NX (manufactured by Johnson & Johnson) advanced course, the sheet-like sample was subjected to a hydrogen peroxide plasma sterilization treatment at room temperature. Using a sheet-like sample (I) before the sterilization treatment and a sheet-like sample (II) repeatedly subjected to the hydrogen peroxide plasma sterilization treatment 100 times as test pieces, a tensile test was performed with an Autograph AGS-X at a tensile speed of 20 mm/min and a chuck distance of 20 mm.

The percentage of a breaking strength of the sheet-like sample (II) relative to a breaking strength of the sheet-like sample (I) (100×[breaking strength of sheet-like sample (II)]/[breaking strength of sheet-like sample (I)]) was determined as a breaking strength retention, and sterilization treatment resistance was evaluated according to the following evaluation criteria.

Evaluation Criteria of Sterilization Treatment Resistance

A: The breaking strength retention is 95% or more.

B: The breaking strength retention is 90% or more and less than 95%.

C: The breaking strength retention is 85% or more and less than 90%.

D: The sheet-like sample is degraded and broken during a sterilization treatment.

The results are shown in Tables below.

TABLE 1

| | (A) Epoxy resin | | (B) Polyamine compound | | (C) Alcohol compound | | | | | Evaluation results | | |
|---|---|---|---|---|---|---|---|---|---|---|---|---|
| | Type | Parts by mass | Type | Parts by mass | Type | Molecular weight | Hydroxyl equivalent | CLogP | Parts by mass | Initial curability | Compatibility | Sterilization treatment resistance |
| Example 1 | A-2 | 100 | B-I-7 | 38 | C-I-1 | 76 | 38 | −0.47 | 3 | A | B | A |
| Example 2 | A-2 | 100 | B-I-7 | 38 | C-I-2 | 74 | 74 | 0.97 | 10 | B | A | A |
| Example 3 | A-2 | 100 | B-I-7 | 38 | C-I-3 | 102 | 102 | 1.8 | 6 | C | B | B |
| Example 4 | A-2 | 100 | B-I-7 | 38 | C-I-4 | 62 | 31 | −0.79 | 6 | C | B | B |
| Example 5 | A-2 | 100 | B-I-7 | 38 | C-I-5 | 118 | 59 | 0.85 | 6 | A | A | A |
| Example 6 | A-2 | 100 | B-I-7 | 38 | C-I-6 | 118 | 59 | 0.6 | 12 | A | A | A |
| Example 7 | A-2 | 100 | B-I-7 | 38 | C-I-7 | 136 | 34 | −1.7 | 16 | B | C | B |
| Example 8 | A-2 | 100 | B-I-7 | 38 | C-I-8 | 92 | 30 | −1.33 | 6 | B | B | B |
| Example 9 | A-2 | 100 | B-I-7 | 38 | C-I-9 | 132 | 66 | 1.26 | 12 | A | A | A |
| Example 10 | A-2 | 100 | B-I-7 | 38 | C-I-10 | 134 | 45 | −0.22 | 10 | S | A | A |
| Example 11 | A-2 | 100 | B-I-7 | 38 | C-I-12 | 108 | 108 | 1.46 | 10 | C | B | C |
| Example 12 | A-2 | 100 | B-I-7 | 38 | C-I-15 | 104 | 52 | 0.43 | 12 | A | A | A |
| Example 13 | A-2 | 100 | B-I-7 | 38 | C-I-19 | 202 | 101 | 3.35 | 10 | C | B | C |
| Example 14 | A-2 | 100 | B-I-7 | 38 | C-I-20 | 15000 | 76 | −0.47 | 10 | A | B | A |
| Example 15 | A-2 | 100 | B-I-7 | 38 | C-I-22 | 16000 | 81 | 0.07 | 10 | A | B | B |
| Example 16 | A-2 | 100 | B-I-7 | 38 | C-I-23 | 5000 | 132 | 0.66 | 15 | B | B | B |
| Example 17 | A-2 | 100 | B-I-7 | 29 | C-I-25 | 75000 | 76 | −0.47 | 3 | B | B | C |
| Example 18 | A-2 | 100 | B-I-1 | 15 | C-I-5 | 118 | 59 | 0.85 | 6 | A | A | B |
| Example 19 | A-2 | 100 | B-I-2 | 29 | C-I-5 | 118 | 59 | 0.85 | 6 | A | A | B |
| Example 20 | A-2 | 100 | B-I-3 | 21 | C-I-5 | 118 | 59 | 0.85 | 6 | A | A | B |
| Example 21 | A-2 | 100 | B-I-4 | 17 | C-I-5 | 118 | 59 | 0.85 | 6 | A | A | B |
| Example 22 | A-2 | 100 | B-I-5 | 16 | C-I-5 | 118 | 59 | 0.85 | 6 | A | A | B |
| Example 23 | A-2 | 100 | B-I-6 | 53 | C-I-5 | 118 | 59 | 0.85 | 6 | A | A | A |
| Example 24 | A-2 | 100 | B-I-8 | 17 | C-I-5 | 118 | 59 | 0.85 | 6 | A | A | B |
| Example 25 | A-2 | 100 | B-I-9 | 14 | C-I-5 | 118 | 59 | 0.85 | 6 | A | B | B |
| Example 26 | A-2 | 100 | B-I-10 | 28 | C-I-5 | 118 | 59 | 0.85 | 6 | A | B | B |

TABLE 2

| | (A) Epoxy resin | | (B) Polyamine compound | | (C) Alcohol compound | | | | | Evaluation results | | |
|---|---|---|---|---|---|---|---|---|---|---|---|---|
| | Type | Parts by mass | Type | Parts by mass | Type | Molecular weight | Hydroxyl equivalent | CLogP | Parts by mass | Initial curability | Compatibility | Sterilization treatment resistance |
| Example 27 | A-2 | 100 | B-I-11 | 18 | C-I-5 | 118 | 59 | 0.85 | 6 | B | B | B |
| Example 28 | A-2 | 100 | B-6 | 24 | C-I-5 | 118 | 59 | 0.85 | 6 | A | B | B |
| Example 29 | A-2 | 100 | B-7 | 43 | C-I-5 | 118 | 59 | 0.85 | 6 | A | B | B |
| Example 30 | A-2 | 100 | B-24 | 10 | C-I-5 | 118 | 59 | 0.85 | 6 | A | B | B |
| Example 31 | A-2 | 100 | B-39 | 12 | C-I-5 | 118 | 59 | 0.85 | 6 | A | B | B |
| Example 32 | A-1 | 100 | B-I-7 | 42 | C-I-10 | 134 | 45 | −0.22 | 10 | S | A | B |
| Example 33 | A-3 | 100 | B-I-7 | 31 | C-1-10 | 134 | 45 | −0.22 | 10 | S | A | B |
| Example 34 | A-4 | 100 | B-I-7 | 42 | C-1-10 | 134 | 45 | −0.22 | 10 | S | A | B |
| Example 35 | A-5 | 100 | B-I-7 | 42 | C-1-10 | 134 | 45 | −0.22 | 10 | S | A | B |
| Example 36 | A-2 | 100 | B-I-12 | 200 | C-1-10 | 134 | 45 | −0.22 | 10 | A | A | A |
| Comparative Example 1 | A-2 | 100 | B-1-7 | 39 | none | — | — | — | — | D | A | D |
| Comparative Example 2 | A-2 | 100 | B-1-7 | 39 | X-1 | 84 | — | −0.18 | 10 | D | C | D |
| Comparative Example 3 | A-2 | 100 | B-1-7 | 39 | X-1 | 84 | — | −0.18 | 25 | D | D | D |
| Comparative Example 4 | A-2 | 100 | B-1-7 | 39 | X-2 | 168 | — | 1.44 | 10 | D | A | D |
| Comparative Example 5 | A-2 | 100 | B-1-7 | 39 | X-2 | 168 | — | 1.44 | 25 | D | A | D |
| Comparative Example 6 | A-2 | 100 | B-1-7 | 39 | X-3 | 110 | — | 1.28 | 10 | D | B | D |
| Comparative Example 7 | A-2 | 100 | B-1-7 | 39 | X-3 | 110 | — | 1.28 | 25 | D | C | D |
| Comparative Example 8 | A-2 | 100 | B-1-7 | 39 | X-4 | 544 | — | 2.18 | 10 | D | A | D |
| Comparative Example 9 | A-2 | 100 | B-1-7 | 39 | X-4 | 544 | — | 2.18 | 25 | D | A | D |
| Comparative Example 10 | A-2 | 100 | B-1-7 | 39 | X-5 | 262 | — | | 10 | D | C | D |

TABLE 2-continued

| | (A) Epoxy resin | | (B) Polyamine compound | | (C) Alcohol compound | | | | Evaluation results | | |
|---|---|---|---|---|---|---|---|---|---|---|---|
| | Type | Parts by mass | Type | Parts by mass | Type | Molecular weight | Hydroxyl equivalent | CLogP | Parts by mass | Initial curability | Compatibility | Sterilization treatment resistance |
| Comparative Example 11 | A-2 | 100 | B-1-7 | 39 | X-5 | 262 | — | | 25 | D | C | D |
| Comparative Example 12 | A-2 | 100 | B-1-7 | 39 | X-6 | 172 | — | 1.64 | 10 | D | A | D |
| Comparative Example 13 | A-2 | 100 | B-1-7 | 39 | X-6 | 172 | — | 1.64 | 25 | D | A | D |
| Comparative Example 14 | A-2 | 100 | B-1-7 | 39 | X-7 | 118 | — | −0.43 | 10 | D | C | D |
| Comparative Example 15 | A-2 | 100 | B-1-7 | 39 | X-7 | 118 | — | −0.43 | 25 | D | C | D |

(A) Epoxy Resin
A-1:
Bisphenol A diglycidyl ether (trade name "jER825", manufactured by Mitsubishi Chemical Corporation, Epoxy Equivalent: 170)
A-2:
Bisphenol A diglycidyl ether (trade name "jER828", manufactured by Mitsubishi Chemical Corporation, epoxy equivalent: 190)
A-3:
Bisphenol A diglycidyl ether (trade name "jER834", manufactured by Mitsubishi Chemical Corporation, epoxy equivalent: 230)
A-4:
Bisphenol F diglycidyl ether (trade name "EPICLON 830", manufactured by DIC Corporation, epoxy equivalent: 170)
A-5:
Phenol novolac epoxy resin (epoxy novolac resin) (product number 406775, manufactured by Sigma-Aldrich, epoxy equivalent: 170)
(B) Polyamine Compound
B-I-1:
1,6-Hexanediamine (manufactured by Tokyo Chemical Industry Co., Ltd., active hydrogen equivalent: 29)
(Specific exemplary polyamine compound B-45 given above)
B-I-2:
1,12-Dodecanediamine (manufactured by Tokyo Chemical Industry Co., Ltd., active hydrogen equivalent: 50)
(Specific exemplary polyamine compound B-49 given above)
B-I-3:
Trimethylhexamethylenediamine (manufactured by Tokyo Chemical Industry Co., Ltd., active hydrogen equivalent: 40)
(Specific exemplary polyamine compound B-46 given above)
B-I-4:
1,3-Cyclohexanediamine (manufactured by Tokyo Chemical Industry Co., Ltd., active hydrogen equivalent: 29)
(Specific exemplary polyamine compound B-50 given above)
B-I-5:
1,3-Bis(aminomethyl)cyclohexane (manufactured by Mitsubishi Gas Chemical Company, Inc., active hydrogen equivalent: 36)
(Specific exemplary polyamine compound B-47 given above)
B-I-6:
Polyoxyalkylenediamine (trade name: D400, manufactured by Mitsui Fine Chemicals, Inc., active hydrogen equivalent: 100)
B-I-7:
Polyoxyalkylenetriamine (trade name: T403, manufactured by Mitsui Fine Chemicals, Inc., active hydrogen equivalent: 73)
B-I-8:
2-Methylpentamethylenediamine (manufactured by Tokyo Chemical Industry Co., Ltd., active hydrogen equivalent: 29)
(Specific exemplary polyamine compound B-51 given above)
B-I-9:
m-Phenylenediamine (manufactured by Tokyo Chemical Industry Co., Ltd., active hydrogen equivalent: 27)
(Specific exemplary polyamine compound B-48 given above)
B-I-10:
4,4'-Ethylenedianiline (manufactured by Tokyo Chemical Industry Co., Ltd., active hydrogen equivalent: 53)
(Specific exemplary polyamine compound B-52 given above)
B-I-11:
m-Xylylenediamine (manufactured by Tokyo Chemical Industry Co., Ltd., active hydrogen equivalent: 34)
(Specific exemplary polyamine compound B-I-11 given above)
B-I-12:
Polyoxyalkylenediamine (trade name: D2000, manufactured by Mitsui Fine Chemicals, Inc., active hydrogen equivalent: 500)
B-6:
Specific exemplary polyamine compound B-6 given above
B-7:
Specific exemplary polyamine compound B-7 given above
B-24:
Specific exemplary polyamine compound B-24 given above
B-39:
Specific exemplary polyamine compound B-39 given above (C) Alcohol Compound (The numbers below correspond to the numbers of the specific exemplary alcohol compounds given above.)

C-I-1:
Propylene glycol (manufactured by Tokyo Chemical Industry Co., Ltd.)

C-I-2:
1-Butanol (manufactured by Tokyo Chemical Industry Co., Ltd.)

C-I-3:
1-Hexanol (manufactured by Tokyo Chemical Industry Co., Ltd.)

C-I-4:
Ethylene glycol (manufactured by Tokyo Chemical Industry Co., Ltd.)

C-I-5:
1,2-Hexanediol (manufactured by Tokyo Chemical Industry Co., Ltd.)

C-I-6:
1,6-Hexanediol (manufactured by Tokyo Chemical Industry Co., Ltd.)

C-I-7:
Pentaerythritol (manufactured by Tokyo Chemical Industry Co., Ltd.)

C-I-8:
Glycerol (manufactured by Tokyo Chemical Industry Co., Ltd.)

C-I-9:
2,2-Diethyl-1,3-propanediol (manufactured by Aldrich)

C-I-10:
Trimethylolpropane (manufactured by Tokyo Chemical Industry Co., Ltd.)

C-I-12:
Benzyl alcohol (manufactured by Tokyo Chemical Industry Co., Ltd.)

C-I-15:
Neopentyl glycol (manufactured by Tokyo Chemical Industry Co., Ltd.)

C-I-19:
1,2-Dodecanediol (manufactured by Tokyo Chemical Industry Co., Ltd.)

C-I-20:
Polyvinyl alcohol (trade name: POVAL PVA103, manufactured by Kuraray Co., Ltd.)

C-I-22:
Synthesized by a method described in Polymer Chemistry, Vol. 16, No. 168, p. 1959.

C-I-23:
Poly(2-hydroxyethyl methacrylate) (number average molecular weight: 5,000, manufactured by Aldrich)

C-I-25:
Polyvinyl alcohol (trade name: POVAL PVA117, manufactured by Kuraray Co., Ltd.)

Other Cure Accelerating Components

X-1:
Dicyandiamide (manufactured by Tokyo Chemical Industry Co., Ltd.)

X-2:
4-Methylhexahydrophthalic anhydride/hexahydrophthalic anhydride=70/30 (trade name: RIKACID MH-700, manufactured by New Japan Chemical Co., Ltd.)

X-3:
2-Ethyl-4-methylimidazole (manufactured by Tokyo Chemical Industry Co., Ltd.)

X-4:
Pentaerythritol tetrakis(3-mercaptobutyrate) (trade name: Karenz MT, manufactured by Showa Denko K.K.)

X-5:
Triphenylphosphine (manufactured by Tokyo Chemical Industry Co., Ltd.)

X-6:
N,N,N',N'-Tetramethyl-1,6-hexanediamine (manufactured by Tokyo Chemical Industry Co., Ltd.)

X-7:
1-Methyl-3-nitroguanidine (manufactured by Tokyo Chemical Industry Co., Ltd.)

Structures of X-1 to X-7 are shown below.

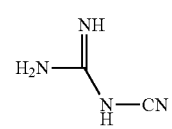

X-1

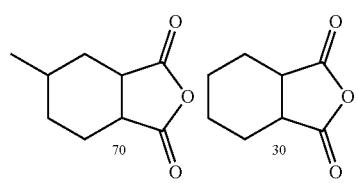

X-2

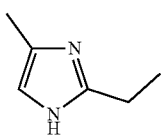

X-3

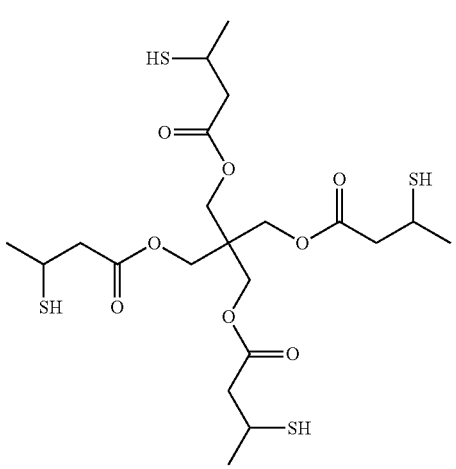

X-4

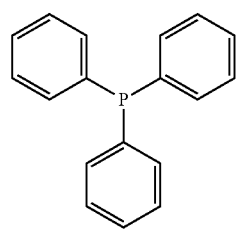

X-5

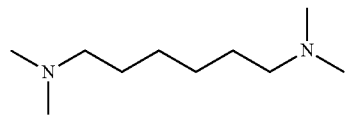

X-6

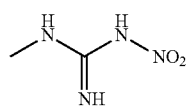

As shown in Tables above, even in the case of an epoxy adhesive including a polyamine compound as a curing component, when a component for accelerating curing reaction was not used or a known cure accelerating component other than alcohol compounds was used, the adhesive had low curability in low-temperature curing reaction, and the resulting cured product had low resistance to sterilization treatments (Comparative Examples 1 to 15).

By contrast, when a polyamine compound serving as a curing component was used in combination with an alcohol compound serving as a cure accelerating component, the adhesive was quickly cured also by low-temperature curing reaction, and the resulting cured product had high resistance to sterilization treatments (Examples 1 to 36). Furthermore, when an alcohol compound was used as a cure accelerating component, the compatibility with an epoxy resin was good, and the resulting cured product had desired transparency (Examples 1 to 36).

While the present invention has been described in connection with embodiments thereof, we do not intend to limit our invention in any detail of the description unless otherwise specified. Rather, the invention should be broadly construed without departing from the spirit and scope of the invention as defined by the appended claims.

This application claims priority from JP2018-131088 filed in Japan on Jul. 10, 2018, the contents of which are hereby incorporated herein by reference as part of this specification.

REFERENCE SIGNS LIST 2 electronic endoscope (endoscope)
3 insertion section
3a flexible tube
3b angle portion
3c tip portion
5 main-body operation section
6 universal cord
11 spiral tube
11a metal strip
12 tubular net
13 cap
14 flexible tube substrate
14a distal side
14b proximal side
15 resin layer
16 coat layer
17 adhesive cured product layer
31 illumination window
32 observation window
33 forceps port
34 nozzle
35 tip-portion main body
36 end cap
37 lens holder
38 prism
39 substrate
40 solid-state imaging element
41 adhesive cured product
42 adhesive cured product
43 observation unit

What is claimed is:

1. An adhesive for an endoscope, comprising:
an epoxy resin including at least one of a bisphenol A epoxy resin, a bisphenol F epoxy resin, or a phenol novolac epoxy resin;
a polyamine compound; and
an alcohol compound,
wherein the alcohol compound is a polymer and has a number average molecular weight of 2,000 to 100,000.

2. The adhesive for an endoscope according to claim 1, wherein the alcohol compound has a hydroxyl equivalent of 25 to 150.

3. The adhesive for an endoscope according to claim 1, wherein the alcohol compound has a CLogP of −1.5 to 3.5.

4. The adhesive for an endoscope according to claim 1, wherein the alcohol compound is a polyol compound.

5. The adhesive for an endoscope according to claim 1, wherein the polyamine compound has an active hydrogen equivalent of 10 to 2,000.

6. The adhesive for an endoscope according to claim 1, wherein the polyamine compound has a polyoxyalkylene structure.

7. The adhesive for an endoscope according to claim 1, wherein, relative to 100 parts by mass of a content of the epoxy resin, a content of the polyamine compound is 5 to 60 parts by mass, and a content of the alcohol compound is 1 to 20 parts by mass.

8. A cured product formed by curing the adhesive for an endoscope according to claim 1.

9. An endoscope comprising the cured product according to claim 8 and a constituent member fixed with the cured product.

10. A method for producing an endoscope, the method comprising fixing a constituent member by using the adhesive for an endoscope according to claim 1.

* * * * *